(12) United States Patent
Cass

(10) Patent No.: US 10,975,410 B2
(45) Date of Patent: *Apr. 13, 2021

(54) DUAL MEDIATOR BIOSENSOR

(71) Applicant: AQUAFFIRM LIMITED, Richmond (GB)

(72) Inventor: Anthony Edward George Cass, London (GB)

(73) Assignee: AQUAFFIRM LIMITED, Richmond (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/763,654

(22) PCT Filed: Sep. 30, 2016

(86) PCT No.: PCT/GB2016/053058
§ 371 (c)(1),
(2) Date: Mar. 27, 2018

(87) PCT Pub. No.: WO2017/055873
PCT Pub. Date: Apr. 6, 2017

(65) Prior Publication Data
US 2018/0282777 A1     Oct. 4, 2018

(30) Foreign Application Priority Data

Sep. 30, 2015 (GB) .................................. 1517275

(51) Int. Cl.
| | | |
|---|---|---|
| *C12Q 1/00* | (2006.01) | |
| *C12Q 1/26* | (2006.01) | |
| *G01N 27/327* | (2006.01) | |

(52) U.S. Cl.
CPC ............ *C12Q 1/004* (2013.01); *C12Q 1/005* (2013.01); *C12Q 1/26* (2013.01); *C12Y 120/02001* (2013.01); *C12Y 120/99001* (2013.01); *G01N 27/3272* (2013.01)

(58) Field of Classification Search
None
See application file for complete search history.

(56) References Cited

U.S. PATENT DOCUMENTS 9,447,384 B2 * 9/2016 Cass .............. C12Y 120/09001
2007/0295616 A1 12/2007 Harding et al.
2013/0026050 A1 1/2013 Harding et al.

FOREIGN PATENT DOCUMENTS

EP          2573190       3/2013
WO    WO 2013/057515    4/2013

OTHER PUBLICATIONS

Male et al. (Keith B. Male et al: "Biosensor for Arsenite Using Arsenite Oxidase and Multiwalled Carbon Nanotube Modified Electrodes", Analytical Chemistry, vol. 79, No. 20, Oct. 1, 2007, pp. 7831-7837).*
Kalimuthu et al. (Electrochemically driven catalysis of *Rhizobium* sp. NT-26 arsenite oxidase with its native electron acceptor cytochrome c552, Biochimica et Biophysica Acta 1837 (2014) 112-120).*
Lleutaud et al. (Arsenite Oxidase from *Ralstonia* sp. 22, The Journal of Biological Chemistry vol. 285, No. 27, pp. 20433-20441, Jul. 2, 2010).*
Santini et al. (The NT-26 cytochrome c552 and its role in arsenite oxidation, Biochimica et Biophysica Acta 1767 (2007) 189-196).*
Male et al. ("Biosensor for Arsenite Using Arsenite Oxidase and Multiwalled Carbon Nanotube Modified Electrodes", Analytical Chemistry, vol. 79, No. 20, Oct. 1, 2007, pp. 7831-7837).*

\* cited by examiner

*Primary Examiner* — Suzanne M Noakes
*Assistant Examiner* — Jae W Lee
(74) *Attorney, Agent, or Firm* — Myers Bigel, P.A.

(57) ABSTRACT

The present invention is a device for detecting the presence of an analyte in a sample. The device comprises (i) at least one electrode, (ii) an oxidase enzyme, and (iii) first and second redox mediators.

22 Claims, 9 Drawing Sheets

Specification includes a Sequence Listing.

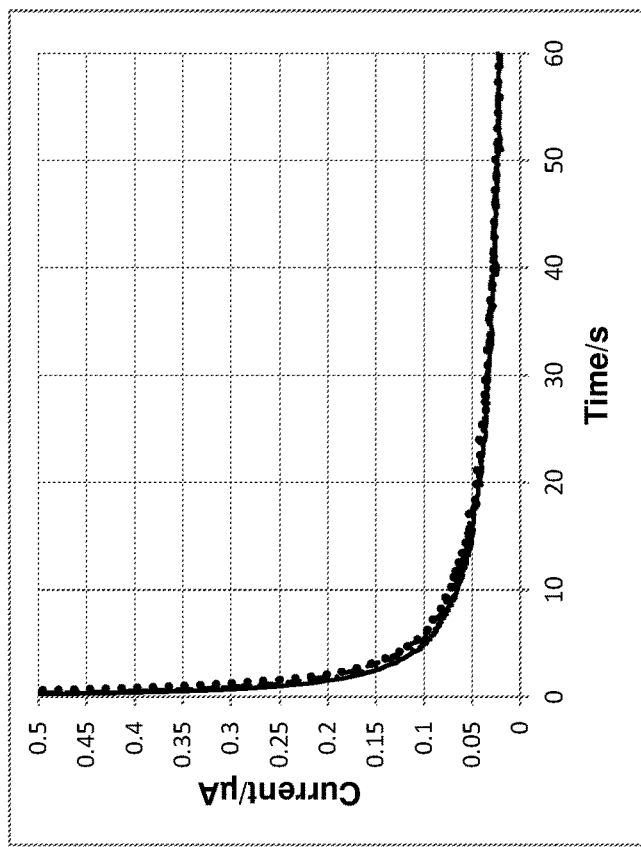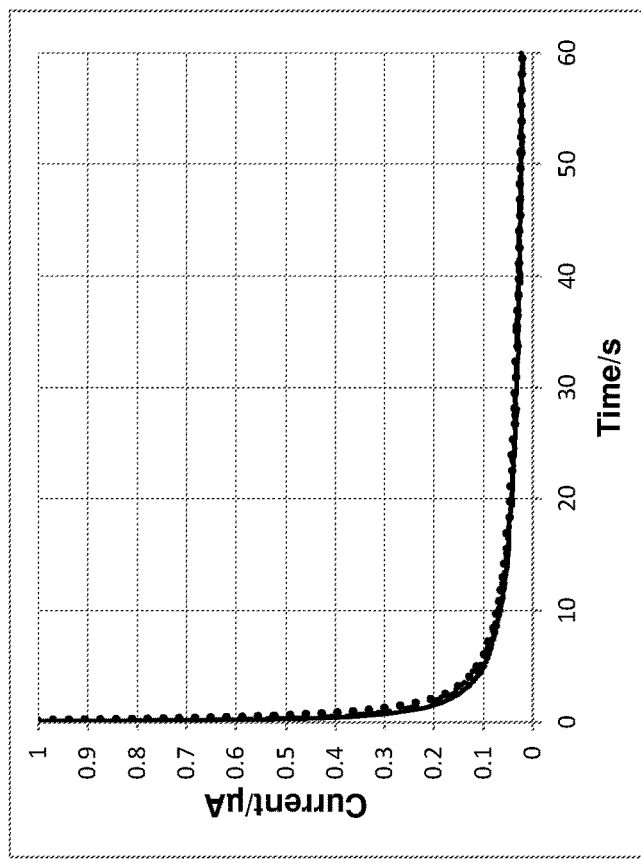
Figure 2a
Figure 2b
— $K_3[Fe(CN)_6]$ + Aio + 0ppb Arsenite
······· $K_3[Fe(CN)_6]$ + Aio + 250ppb Arsenite
— — $K_3[Fe(CN)_6]$ + Aio + 500ppb Arsenite
— · — $K_3[Fe(CN)_6]$ + Aio + 750 ppb Arsenite — $K_3[Fe(CN)_6]$ + Aio + 0ppb Arsenite ·········· $K_3[Fe(CN)_6]$ + Aio + 250ppb Arsenite — — $K_3[Fe(CN)_6]$ + Aio + 500ppb Arsenite — · — $K_3[Fe(CN)_6]$ + Aio + 750 ppb Arsenite ——— Horse heart cytochrome C + Aio + 0ppb Arsenite ·········· Horse heart cytochrome C + Aio + 250ppb Arsenite — — Horse heart cytochrome C + Aio + 500ppb Arsenite — · — Horse heart cytochrome C + Aio + 750 ppb Arsenite ——— Ferricyanide + Horse heart cytochrome C + Aio + 0ppb Arsenite ·········· Ferricyanide + Horse heart cytochrome C + Aio + 250ppb Arsenite — — Ferricyanide + Horse heart cytochrome C + Aio + 500ppb Arsenite — · — Ferricyanide + Horse heart cytochrome C + Aio + 750 ppb Arsenite ◆ Ferricyanide + Aio ■ Horse heart cytochrome C + Aio ▲ Ferricyanide + Horse heart cytochrome C + Aio

DUAL MEDIATOR BIOSENSOR

STATEMENT OF PRIORITY

This application is a 35 U.S.C. § 371 national phase application of International Application Serial No. International App. No.: PCT/GB2016/053058, filed Sep. 30, 2016, which claims the benefit, under 35 U.S.C. § 119 (a) of Great Britain Application No. 1517275.2, filed Sep. 30, 2015, the entire contents of each of which are incorporated by reference herein.

STATEMENT REGARDING ELECTRONIC FILING OF A SEQUENCE LISTING

A Sequence Listing in ASCII text format, submitted under 37 C.F.R. § 1.821, entitled 1476-2_Seq_List, 15970 bytes in size, generated on Mar. 27, 2018 and, filed via EFS-Web, is provided in lieu of a paper copy. This Sequence Listing is hereby incorporated by reference herein into the specification for its disclosures.

FIELD OF THE INVENTION

The present invention relates to a biosensor comprising a dual electron acceptor system. The invention is also directed to uses of the biosensor for detecting an analyte, in particular arsenic derivatives such as arsenite, in a sample.

BACKGROUND TO THE INVENTION

It is said that the third major challenge for a sustainable future (together with food security and energy) will be making the best use of limited supplies of pure water for both agricultural use and human consumption, and the remediation of marginal and contaminated water will be essential in achieving this. Already groundwater contamination, resulting from either natural geochemical processes or industrial activities such as mining, is a major problem in many countries.

Arsenic (As) is a groundwater contaminant that is ubiquitous in the environment and the two soluble forms, arsenite ($As^{III}$) and arsenate ($As^{V}$), are toxic. Anthropogenic activity has resulted in widespread contamination of both soluble forms but $As^{III}$ is prevalent in anoxic environments, including most sources of drinking water. Countries affected include India, Bangladesh, Vietnam, USA, Germany, France, Hungary, Australia, Argentina, Mexico, Canada.

An important aspect of remediation is assessment and monitoring, and whilst laboratory methods exist that demonstrate high specificity and sensitivity (e.g. ICP-MS or HPLC) it is also possible, and indeed desirable, to measure analytes such as arsenite in the field using sensors. Ideally, the sensors should be low-cost, disposable and able to be readily adapted to multiple analytes that are commonly found together in contaminated water.

Many As field test kits are commercially available (e.g. from Industrial Systems, Inc, Hydrodyne) but these only detect total As, rather than the most toxic form, $As^{III}$, which is dominant in anoxic drinking waters. Moreover, because As remediation preferentially removes $As^{V}$ (e.g. by binding to iron hydroxide) and requires the pre-oxidation of $As^{III}$, it is crucial to determine whether any $As^{III}$ remains in the water. The chemically based arsenic field kits rely on a colorimetric method which reduces the $As^{III}$ and $As^{V}$ to the gas arsine which reacts with the mercuric bromide test strips. These kits require the training of personnel, are expensive (e.g. Arsenic, Quick II Hydrodyne kit US$4.24 per test and Ultra Low Quick II, Industrial Test Systems, Inc. US$6 per test) and have low sensitivity and reproducibility.

Whole cell biosensors have been developed for the detection of $As^{III}$ by a number of groups (e.g. Stocker et al. (2003) Environ. Sci. Technol. 37, 4743-4750). These methods are all based on colorimetric assays that sometimes require the use of a luminometer. They all use the regulatory mechanism of the *Escherichia coli* arsenic resistance system which detects both $As^{III}$ and antimonite ($Sb^{III}$). The regulatory gene in this system, arsR, is fused to a reporter gene (e.g. luciferase gene, luxB) that when expressed after induction with $As^{III}$ produces a visible signal (e.g. fluorescence).

There are many problems with whole cell based $As^{III}$ biosensors, including: 1) the system is too complex and because of this has a slow response time (i.e. $As^{III}$ must enter cells followed by induction of regulator-reporter gene protein this can take up to 24 hours for a response); 2) lack of specificity as the system does not discriminate between $As^{III}$ and SIP; 3) incubation temperatures of 30° C. are often required; 4) colorimetric assay often requires use of a luminometer, which is not feasible at most field sites; and 5) use of genetically modified organisms always presents an additional problem. No whole cell biosensors for the detection of $As^{III}$ are commercially available.

A biosensor for $As^{III}$ has been developed using molybdenum-containing arsenite oxidase (known as "Aio" and also previously known as Aro and Aso; see Lett et al., Unified Nomenclature for Genes Involved in Prokaryotic Aerobic Arsenite Oxidation; J. Bacteriology, 4 Nov. 2011; p. 207-208) which is a member of the DMSO reductase family, prepared from chemolithoautotrophic Alphaproteobacterium *Rhizobium* sp. strain NT-26 (Santini et al. (2000) Appl. Environ. Microbiol. 66, 92-97).

$As^{III}$ oxidase catalyses the oxidation of $As^{III}$ to $As^{V}$ and the suitability of this native enzyme for use as a biosensor has been tested and shown to detect down to 1 ppb $As^{III}$, which is 10 times lower than the recommended WHO MCL (maximum contaminant level) of As in drinking water. Furthermore the native enzyme shows specificity for $As^{III}$ (Male et al. (2007) Anal. Chem. 79, 7831-7837). The biosensor comprises the enzyme directly linked to the surface of a mulitwalled carbon nanotube-modified electrode, in which electron transfer proceeds directly from enzyme to electrode. The authors noted, however, that certain commonly-used electrode materials, in particular glassy carbon (GC), were not suitable for direct electron transfer in this configuration.

Heterologous expression of molybdenum-containing enzymes, especially members of the DMSO reductase family, is notoriously difficult. Recently, the dissimilatory arsenate reductase from *Shewanella* sp. str. ANA-3 was expressed in *Escherichia coli* but comparisons with the native enzyme were not made (Malasarn et al. (2008) J. Bacteriol. 190, 135-142). Expression was optimal when *E. coli* was grown anaerobically with DMSO although other electron acceptors for anaerobic growth were not tested and neither were different strains.

Since the entire native Aio is poorly expressed in a heterologous expression system, such as *E. coli*, use of this enzyme in routine detection of $As^{III}$ is not commercially viable.

WO2013/057515 discloses a modified arsenite oxidase and a biosensor for detecting arsenite. In this prior art publication, the native arsenite oxidase enzyme $As^{III}$ oxidase from *Rhizobium* sp. NT-26 was modified to prevent translocation to the periplasm. The modified enzyme comprises the native AioA subunit from NT-26, or a variant, homologue or derivative thereof, and the native AioB subunit from NT-26, or a variant, homologue or derivative thereof. Furthermore, a portion of the native AioB subunit corresponding to the translocation signal sequence, or a functional fragment thereof, is modified.

There is still a need in the art for improved sensors for rapid, cheap and effective detection of $As^{III}$ in liquids such as drinking-water, waste-water and biological samples.

SUMMARY OF THE INVENTION

According to a first aspect, the present invention provides a device for detecting the presence of an analyte in a sample, comprising (i) at least one electrode, (ii) an oxidase enzyme, and (iii) first and second redox mediators. Preferably, the enzyme is an arsenite oxidase and the analyte is arsenite ($As^{III}$).

According to a second aspect, the present invention is directed to the use of a device according to the first aspect of the invention as a biosensor to detect the presence of $As^{III}$ in a sample. Preferably, the sample has a neutral pH of around 7.

According to a third aspect, the present invention provides an electrochemical system comprising an oxidase enzyme, an electrode and two redox mediators. Preferably, the enzyme is an arsenite oxidase.

According to a fourth aspect, the present invention is directed to the use of an electrochemical system according to the third aspect of the invention to increase the overall reaction rate of a biosensor. Preferably, the biosensor is an arsenite biosensor.

DESCRIPTION OF THE FIGURES

FIG. 2a shows the chronoamperometry results for experiment 1. FIG. 2b is a magnified plot of FIG. 2a.

FIG. 4a shows the chronoamperometry results for experiment 2. FIG. 4b is a magnified plot of FIG. 4a.

FIG. 6a shows the chronoamperometry results for experiment 3. FIG. 6b is a magnified plot of FIG. 6a.

DETAILED DESCRIPTION OF THE INVENTION

Figure 1:
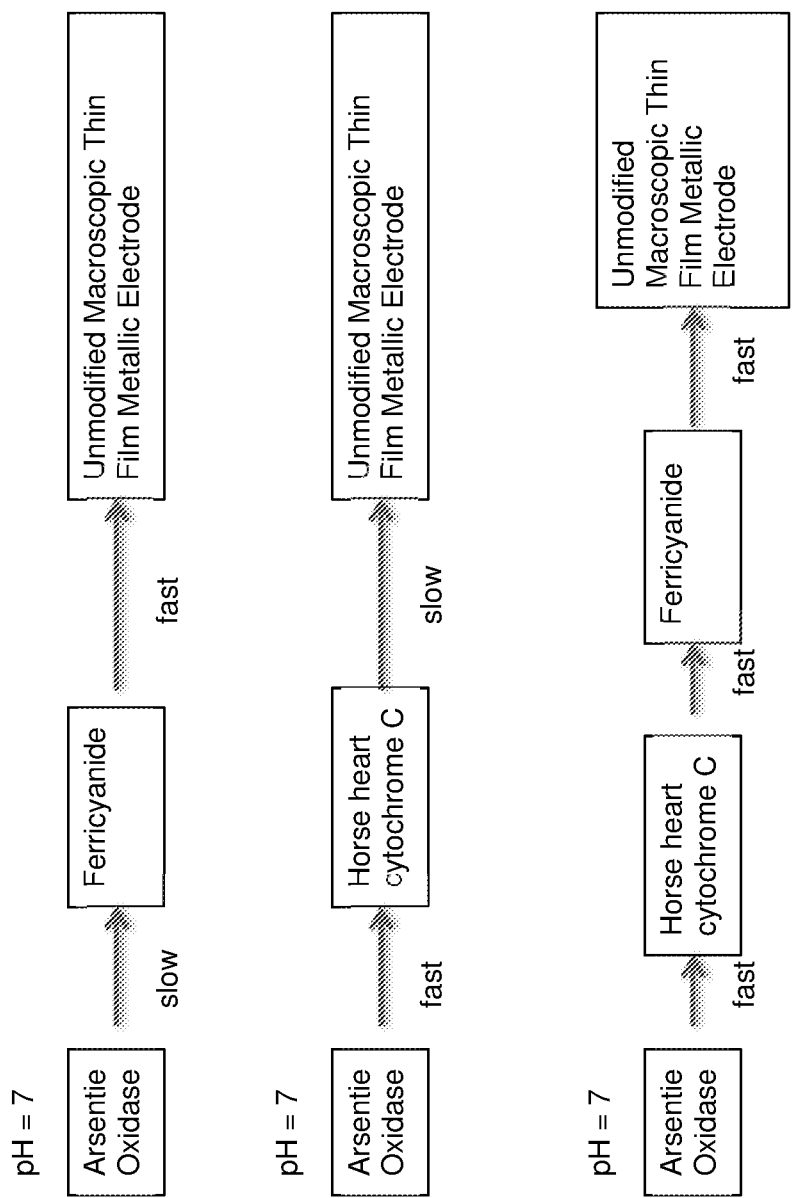
FIG. 1 is an illustration of how including two redox mediators in an arsenic biosensor increases the overall reaction rates of the device at neutral pH.

The present inventors previously developed a modified version of the native $As^{III}$ oxidase from *Rhizobium* sp. NT-26 (GenBank Accession Number AY345225) which can be successfully expressed in heterologous expression systems such as *E. coli*. The modified arsenite oxidase (Aio-NT26) oxidises arsenite ($As^{III}$) to arsenate ($As^V$). After each oxidation reaction arsenite oxidase can react with a second molecule, a redox mediator, which acts as an electron acceptor, accepting electrons from the arsenite oxidase. Thus, the electron acceptor molecule is reduced and the arsenite oxidase, re-oxidised.

The oxidation of the reduced form of the electron acceptor molecule at an electrode forms the basis of an electrochemical biosensor for arsenite, and such a biosensor is described in WO2013/057515. To produce low-cost disposable biosensors, various electrode materials can be used, including metallic (gold, platinum and palladium) sputtered thin-film electrodes.

In the biosensor described in the prior art, a two-step reaction takes place. Firstly, there is a chemical reaction step between the arsenite oxidase and the electron acceptor. Secondly, there is a heterogeneous electron transfer step, which takes place between the electron acceptor molecule and the electrode.

The present invention is based on the realisation that in such a biosensor it is advantageous for both the chemical reaction step and the heterogeneous electron transfer step to be as fast as possible. In addition, for the purposes of creating a biosensor that detects arsenite levels in water (e.g. drinking water, surface and ground water) it is advantageous if the biosensor works fast at close to neutral pH values.

Potassium ferricyanide is an electron acceptor molecule that has fast electron transfer kinetics with electrodes, such as metallic sputtered thin-film electrodes, making it a good candidate redox mediator for use in an arsenite biosensor. However, at neutral pH (around pH 7) potassium ferricyanide has a slow chemical reaction rate when oxidising arsenite oxidase [Warelow, TP; (2015) Arsenite oxidase as a novel biosensor for arsenite. Doctoral thesis, UCL (University College London)]. The chemical oxidation of arsenite oxidase by potassium ferricyanide works best at acidic values close to pH 4.5. This means that water samples need to have their pH values adjusted to an acidic value by the addition of a suitable buffer, in order for ferricyanide to be used effectively as a redox mediator in an arsenite biosensor such as a biosensor described in WO2013/057515.

In contrast, horse heart cytochrome C has a fast chemical reaction rate when oxidising arsenite oxidase at close to neutral pH values (pH 7). However, it has poor electron transfer kinetics on unmodified macroscopic metallic thin-film electrodes. This means that if cytochrome C is to be used effectively as a redox mediator in a arsenite biosensor such as a biosensor described in WO2013/057515, it is necessary to modify gold thin-film electrodes with a chemical, such as 4,4'-Dipyridyl disulphide, to increase the electron transfer rate between cytochrome C and the electrode.

The present inventors have realised that at pH 7, ferricyanide will chemically oxidise horse heart cytochrome C with a fast reaction rate. Therefore, instead of using a single electron acceptor molecule (ferricyanide or cytochrome C) the inventors have developed a new system in which the overall reaction rates of the biosensor at neutral pH values are increased by using two redox mediators (exemplified as cytochrome C and ferricyanide). This is illustrated in FIG. 1.

Accordingly, a first aspect of the invention provides a device for detecting the presence of an analyte in a sample, comprising (i) at least one electrode, (ii) an oxidase enzyme, and (iii) first and second redox mediators.

The analyte is preferably an arsenic derivative, preferably arsenite ($As^{III}$). The device includes two redox mediators. The term "redox mediator" is defined as any moiety capable of transferring electrons from the enzyme to the electrode surface. Artificial redox mediators such as 2,6-dichlorophenolindophenol (DCPIP) are often used in solution in laboratory-based spectrophotometric measurements; however spectrophotometric measurements are not routinely used in field test equipment.

As explained above, the inclusion of two redox mediators is advantageous, compared with existing devices which comprise only a single redox mediator, or in which the enzyme is directly linked to an electrode. The presence of two redox mediators improves the rate and efficiency of electron transfer through the system from the enzyme to the electrode.

In a first chemical reaction step, the first redox mediator accepts an electron from the enzyme. The first redox mediator then transfers an electron to the second redox mediator (i.e. the first redox mediator is oxidised by the second redox mediator). This is followed by heterogeneous electron transfer between the second redox mediator and the electrode, in which the second redox mediator is oxidised.

The first and second redox mediators may each be independently selected from suitable compounds where the compounds exist in two or more different redox states. Examples include iron, ruthenium, cobalt or osmium complexes such as ferrocene or ferrocene derivatives including ferrocene carboxylic acid, hydroxymethyl ferrocene (ferrocene methanol), and ferricyanide, tris(2,2'-bipyridine)dichlororuthenium(II) and cytochrome C and other redox biological molecules. Examples also include organic molecules that can exist in two or more accessible redox states, for example conducting organic polymers, conducting organic salts, tetrathiafulvalene (TTF) and quinones, 2,6-dichlorophenolindophenol and other dyes. Preferably, the first and second redox mediators are different. Preferably, the first redox mediator is cytochrome C (including but not limited to horse heart cytochrome C). Preferably, the second redox mediator is ferricyanide or a lower potential iron complex.

In one embodiment, the device comprises a test strip made of polymer or ceramic materials. Preferably, the device comprises two or more planar electrodes. Preferably the device comprises a "reference electrode" in addition to the test electrode. At least the test electrode incorporates the $As^{III}$ oxidase.

Advantageously, the device of the invention is versatile and works with a variety of test electrode materials. In a preferred embodiment, the electrode is made of one or more conducting materials, preferably selected from carbon, carbon nanotubes, graphene, graphite, gold, palladium, platinum, glassy carbon, nanostructured metal oxides or nanostructured metal. The electrode may be a metallic spluttered thin-film electrode made of gold, platinum or palladium. Alternatively, the electrode may be an unmodified macroscopic thin film metallic electrode.

Preferably, the reference electrode comprises a reference redox couple, such as Ag/AgCl.

The electrode materials can be deposited on the test strip by a variety methods including, but not limited to, screen-printing or evaporation or sputtering. The electrodes may be open or covered by a lid so forming a defined volume cell. There may, or may not, be a membrane covering the electrodes.

The test strip is suitable for laboratory use and, preferably, field-based use (i.e. $As^{III}$ can be detected in a sample at the source using the test strip or device). The device may be suitable for multiple uses or a single use, and may be disposable.

Preferably, the device comprises a micro-structured surface, with the enzyme entrapped thereon with the two redox mediators. A micro-structured surface, for example pillars rising from the base of the electrode, improves the performance of the electrode.

Preferably the sample in which $As^{III}$ is detected using the device of the invention is a liquid sample. The liquid sample may be any type of liquid that is susceptible to $As^{III}$ contamination, including, but not limited to, ground-water, drinking-water, environmental liquids such as mining effluent and sewage, waste-water, biological samples.

In use, the test sample is brought into direct contact with the test strip. Operation of the sensor device involves applying an electrical potential between the test and reference electrodes and measuring the current. A number of methods would be apparent to those skilled in the art, and include, but are not limited to, chronoamperomerty, square wave voltammetry and coulometry.

The enzyme may be any oxidase, but in a preferred embodiment the enzyme is an arsenite oxidase. Most preferably, the arsenite oxidase enzyme is a modified version of the native $As^{III}$ oxidase from *Rhizobium* sp. NT-26 (GenBank Accession Number AY345225). Such a modified enzyme is disclosed in WO2013/057515. The content of that publication is incorporated by reference herein.

The native $As^{III}$ oxidase consists of two heterologous subunits: AioB is the small subunit largely composed of beta sheets and AioA is the large subunit largely composed of alpha-helices (Santini & van den Hoven (2004) J. Bacteriology. 186(6):1614-1619). The polypeptide sequence of wild-type AioB from *Rhizobium* sp. NT-26 is shown in SEQ ID No. 1 and SEQ ID No. 5 shows the corresponding nucleotide sequence. The AioB subunit comprises a Tat leader sequence (also referred to herein interchangeably as a Tat translocation signal sequence) which corresponds to the first 25 amino acids of SEQ ID No 1. This translocation signal sequence is shown as SEQ ID No. 2 and SEQ ID No. 6 shows the nucleotide sequence of the portion of the aioB gene encoding the translocation signal sequence. The signal sequence directs the transport of the protein to the periplasm using the Twin Arginine Translocation (Tat) pathway.

The native $As^{III}$ oxidase has been modified by modifying the translocation signal sequence in the AioB subunit. As a result of the modification, the modified enzyme is not exported from the host cytoplasm, and as a result can be expressed in large, commercially-viable quantities.

The translocation signal sequence can be modified by various methods which will be apparent to a person skilled in the art, including frame-shift mutations, substitution mutations or deletion. Any modification that results in loss of function of the native translocation signal sequence can be used, however deletion of the translocation signal sequence or a functional fragment thereof, is preferred.

The modified $As^{III}$ oxidase comprises two subunits. The first subunit corresponds to the native AioA subunit from NT-26, or a variant, derivative or homologue thereof. The second subunit corresponds to the native AioB subunit from NT-26, or a variant, derivative or homologue thereof; however a portion of the native AioB subunit which corresponds to the translocation signal sequence, or a functional fragment of the translocation signal sequence, is modified in the enzyme of the invention. Preferably, the portion of the native AioB subunit which corresponds to the translocation signal sequence, or a functional fragment thereof, is modified by deletion.

Preferably, at least a portion of the aioB gene which encodes the translocation signal sequence, or a portion thereof encoding a functional fragment of the translocation signal sequence, is modified, preferably by deletion.

The portion of the aioB gene sequence encoding the translocation signal sequence is identified herein as SEQ ID NO. 6. Either the complete sequence identified as SEQ ID NO. 6 or a homologue of this sequence encoding a functional fragment of the translocation signal sequence may be modified. As a result of the modification to the nucleotide sequence, the modified enzyme of the invention does not comprise the amino acid sequence identified herein as SEQ ID No. 2, or does not comprise a portion thereof that is required for a functional translocation signal sequence.

As used herein, the term 'functional fragment' means that the portion of the nucleotide sequence that is modified (e.g. by deletion) encodes a polypeptide having Tat translocation signal sequence activity, preferably having at least the same activity of the polypeptide shown as SEQ ID NO: 2. As a result of the modification, the recombinant enzyme of the invention lacks such Tat translocation signal sequence activity.

As used herein, the term "homologue" refers to a nucleotide sequence that encodes a polypeptide which has Tat translocation signal sequence activity. With respect to sequence similarity, preferably there is at least 60%, more preferably at least 70%, more preferably at least 75%, more preferably at least 85%, more preferably at least 90% sequence similarity between SEQ ID NO. 6 and the sequence of the native aioB gene that is modified according to the invention. More preferably there is at least 95%, more preferably at least 98%, sequence similarity. These terms also encompass allelic variations of the sequences.

The portion of the aioB gene that is modified may comprise or consist of the sequence identified herein as SEQ ID NO. 6.

SEQ ID No. 3 corresponds to the amino acid sequence of the AioB subunit excluding the entire native leader region. SEQ ID No. 7 shows the corresponding nucleotide sequence. If the entire AioB leader region is deleted, then the AioB subunit of the modified enzyme of the invention will correspond to SEQ ID No. 3. However, a portion of the leader region within the AioB subunit may remain unmodified, provided that the portion of the leader region that is modified renders the remaining portion non-functional.

SEQ ID No. 4 shows the amino acid sequence of the AioA subunit and SEQ ID No. 8 shows the corresponding nucleotide sequence.

The modified $As^{III}$ oxidase may comprise homologues, variants or derivatives of SEQ ID Nos. 3 and 4.

The terms "variant", "homologue", "derivative" or "fragment" as used herein include any substitution, variation, modification, replacement, deletion or addition of one (or more) amino acid from or to a sequence. The variant may have a deletion, insertion or substitution variation. The variation may produce a silent change and a functionally equivalent polypeptide, or may result in improved catalytic function or other characteristics of the resulting enzyme. Deliberate amino acid substitutions may be made on the basis of similar physio-chemical properties such as size, charge and hydrophobicity in order to alter the catalytic function or other properties or characteristics of the enzyme.

Unless the context admits otherwise, references to "AioA" and "AioB" include references to such variants, homologues and derivatives of the native subunits. The term "homologue" covers identity with respect to structure and/or function and is used to refer to peptides that share levels of sequence identity or similarity to SEQ ID Nos. 3 and 4 and retain at least the functionality of the native amino acid sequences. The variants may result in improvements in the catalytic activity or other properties of the resulting enzyme. These terms also encompass polypeptides derived from amino acids which are allelic variations of the aioA and/or aioB nucleic acid sequences (SEQ ID Nos. 7 and 8).

Levels of identity or similarity between amino acid sequences can be calculated using known methods. Publicly available computer based methods include BLASTP, BLASTN and FASTA (Atschul et al., Nucleic Acids Res., 25: 3389-3402 (1997)), the BLASTX program available from NCBI, and the GAP program from Genetics Computer Group, Madison Wis.

It is preferable if there is at least 60% sequence identity or similarity to the specified peptides of SEQ ID Nos. 3 and 4, preferably 70%, more preferably 80% and most preferably greater than 90%, e.g. at least 95% to the sequences of SEQ ID Nos. 3 and 4. The removal of the Tat leader sequence or a functional fragment thereof to prevent export to the periplasm is a known technique, and has been used previously in the production of heterodimeric molybdenum-containing enzymes (Malasarn et al. (2008), J Bacteriol, 190, 135-142). However, $As^{III}$ oxidase differs from other molybdenum-containing enzymes in that it is a much larger $\alpha_2\beta_2$ heterotetramer containing additional co-factors (i.e. a 3Fe-4S cluster and a Rieske 2Fe-2S cluster) not present in other molybdenum-containing enzymes). It has been demonstrated that the native enzyme is localised to the periplasm (Santini et al. (2000), J Bacteriol, 66, 92-97), given size of the assembled heterotetrameric complex it is therefore reasonable to speculate that two $\alpha\beta$ heterodimers formed in the cytoplasm are exported (via the Tat system) to the periplasm prior to heterotetrameric complex formation. Therefore, the present inventors were surprised to find that that following removal of the Tat leader sequence, the modified $As^{III}$ oxidase could achieve complete assembly (both subunit assembly and cofactor addition) to form a heterotetramer in the cytoplasm of the various *E. coli* strains.

For the avoidance of doubt, the abbreviations "aio", "Aio", "aro", "Aro", "aso" and "Aso" can be used interchangeably and all refer to the arsenite oxidase enzyme (gene or protein). The different abbreviations are the result of different nomenclature that has been used in the art (Lett et al., J. Bacteriology, 4 Nov. 2011; p. 207-208).

The advantage of using a modifying $As^{III}$ oxidase is that is can be expressed successfully in heterologous expression systems such as *E. coli* at high, commercially-viable yields. Once expressed, the enzyme can be used to detect the presence of $As^{III}$. The modified enzyme has been found to be equally effective as the native enzyme in catalysing the oxidation of $As^{III}$ to arsenate $As^{V}$ (Warelow & Santini, unpublished data). The absence of the translocation sequence does not impact upon the catalytic activity of the enzyme. The modified enzyme is therefore suitable for use in biosensors to detect the presence of $As^{III}$.

A second aspect of the present invention is directed to the use of a device according to the first aspect of the invention as a biosensor to detect the presence of an analyte, preferably $As^{III}$, in a sample. Preferably, the sample is a liquid sample, having a neutral pH of around 7.

A third aspect of the present invention provides an electrochemical system comprising an oxidase enzyme, an electrode and two redox mediators. Preferably, the oxidase enzyme is arsenite oxidase. Preferably the electrode is as defined above in relation to the first aspect of the invention.

In the electrochemical system according to the third aspect, a first redox mediator accepts an electron from the enzyme and transfers an electron to the second redox mediator. A second redox mediator accepts an electron from the first redox mediator and transfers an electron to the electrode.

The two redox mediators may each be independently selected from suitable compounds where the compounds exist in two or more different redox states. Examples include iron, ruthenium, cobalt or osmium complexes such as ferrocene or ferrocene derivatives including ferrocene carboxylic acid, hydroxymethyl ferrocene (ferrocene methanol), and ferricyanide, tris(2,2'-bipyridine)dichlororuthenium(II) and cytochrome C and other redox biological molecules. Examples also include organic molecules that can exist in two or more accessible redox states, for example conducting organic polymers, conducting organic salts, tetrathiafulvalene (TTF) and quinones, 2,6-dichlorophenolindophenol and other dyes. Preferably, the first and second redox mediators are different. Preferably, the first redox mediator is cytochrome C (including but not limited to horse heart cytochrome C). Preferably, the second redox mediator is ferricyanide or a lower potential iron complex.

A fourth aspect of the present invention is directed to the use of an electrochemical system according to the third aspect of the invention to increase the overall reaction rate of an arsenite biosensor, as described in detail above.

The invention will now be described further with reference to the following non-limiting example.

Example

A homogeneous chemical reaction between one or two mediators, arsenite oxidase (Aio) and arsenite was allowed to run for 60 seconds at room temperature before measuring the reduced form of the second mediator electrochemically, using chronoamperometry.

Disposable thin-film gold sputtered electrode with a 15 mm square working electrode area were used. These were produced by laser ablation. A plastic tape with a 8 mm×8 mm square aperture was attached on top of the electrode to make an open sample cell. Electrochemical measurements were conducted with a PalmSens EmStat potentiostat using a standard three electrode set up, with a Ag/AgCl reference electrode. A new electrode was used for each electrochemical measurement.

Experiment 1

In the sample cell on top of the electrode a 10 microlitre volume of either a 0 ppb, 2500 ppb, 5000 ppb or 7500 ppb aqueous solution of arsenite was added to a 90 microlitre 10 mM phosphate buffer (pH=7.2) solution containing ferricyanide and 0.002028 Units of Aio. This gave final concentrations of 14 micromolar ferricyanide and either 0 ppb, 250 ppb, 500 ppb or 750 ppb arsenite. 60 seconds after mixing a chronoamperometry measurement was made by applying a step potential of 0.5 V vs Ag/AgCl reference electrode and recording data for 60 seconds.

Figure 3:
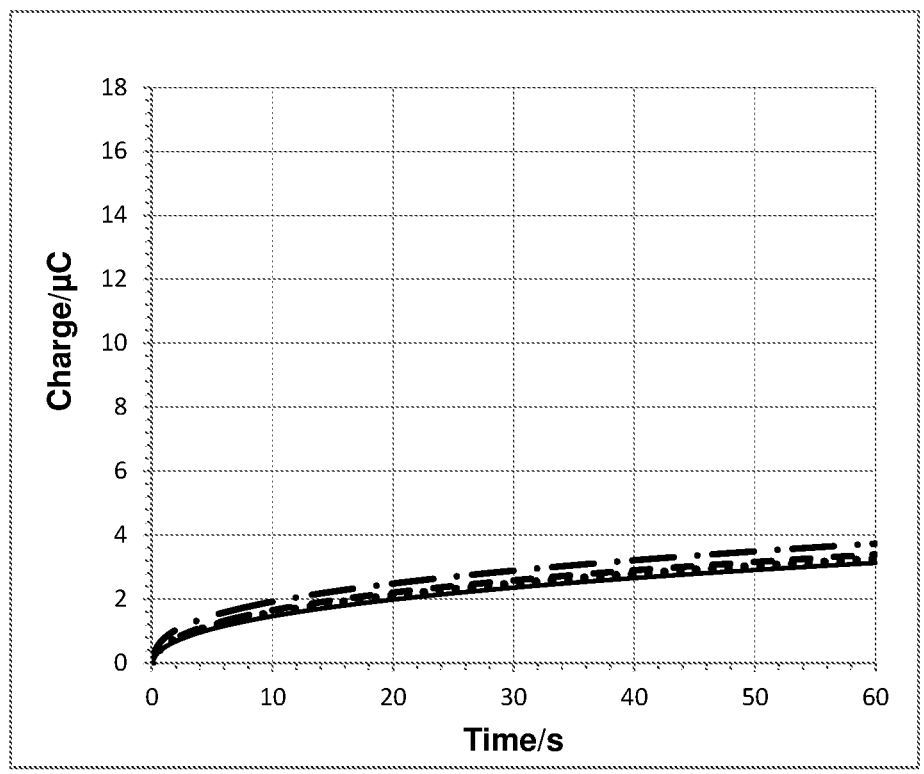
FIG. 3 shows a plot of the integration of the chronoamperometry data shown in FIGS. 2a and 2b.

The chronoamperometry results for experiment 1 are shown in FIGS. 2a and 2b. FIG. 2b is a magnified plot of FIG. 2a. FIG. 3 shows a plot of the integration of the chronoamperometry data shown in FIGS. 2a and 2b.

Experiment 2

In the sample cell on top of the electrode a 10 microlitre volume of either a 0 ppb, 2500 ppb, 5000 ppb or 7500 ppb aqueous solution of arsenite was added to a 90 microlitre 10 mM phosphate buffer (pH=7.2) solution containing horse heart cytochrome C and 0.002028 Units of Aio. This gave final concentrations of 100 nanomolar horse heart cytochrome C and either 0 ppb, 250 ppb, 500 ppb or 750 ppb arsenite. 60 seconds after mixing a chronoamperometry measurement was made by applying a step potential of 0.5 V vs Ag/AgCl reference electrode and recording data for 60 seconds.

Figure 4:
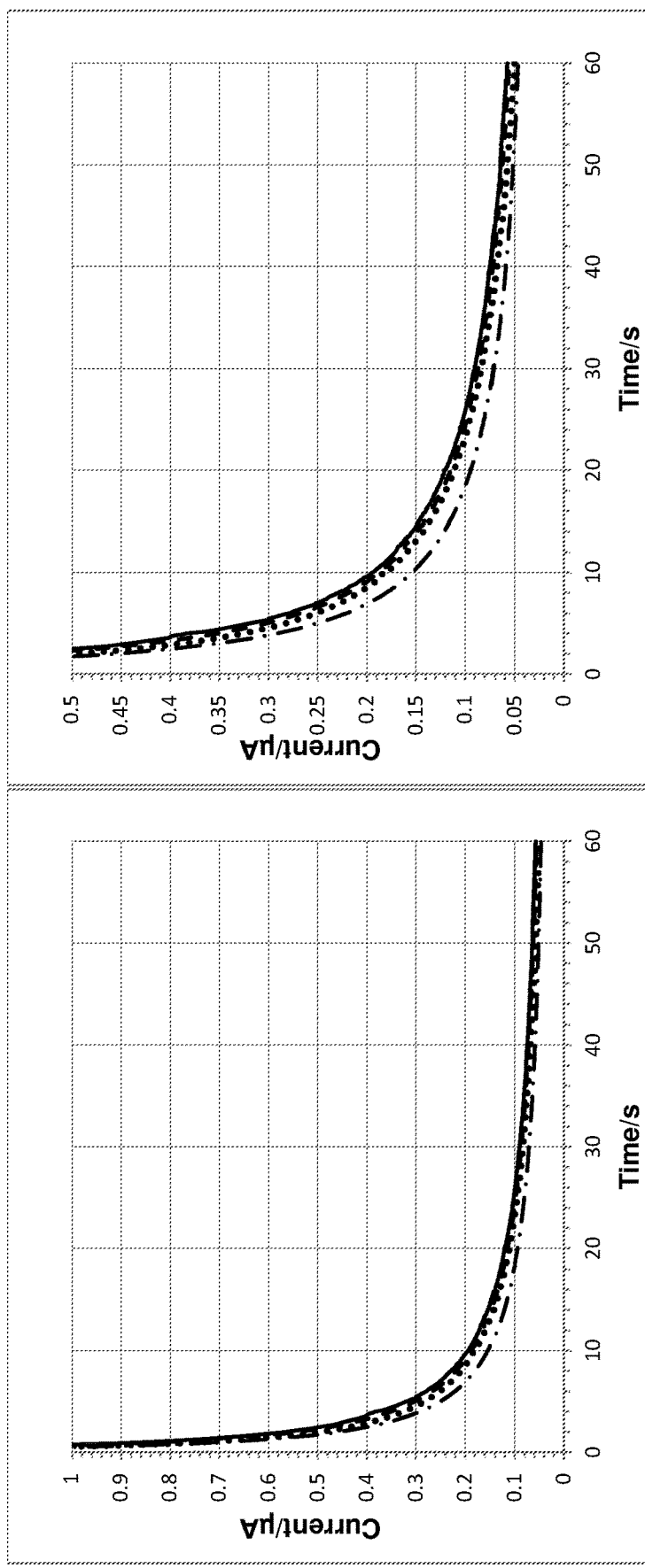
Figure 5:
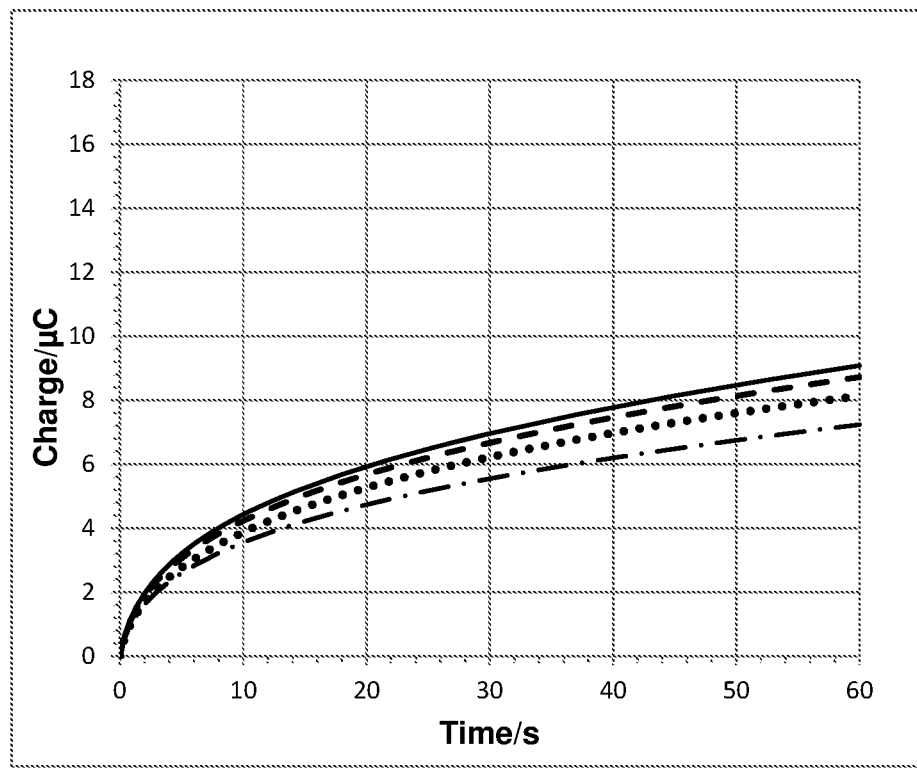
FIG. 5 shows a plot of the integration of the chronoamperometry data shown in FIGS. 4a and 4b.

The chronoamperometry results for experiment 2 are shown in FIGS. 4a and 4b. FIG. 4b is a magnified plot of FIG. 4a. FIG. 5 shows a plot of the integration of the chronoamperometry data shown in FIGS. 4a and 4b.

Experiment 3: In the sample cell on top of the electrode a 10 microlitre volume of either a 0 ppb, 2500 ppb, 5000 ppb or 7500 ppb aqueous solution of arsenite was added to a 90 microlitre 10 mM phosphate buffer (pH=7.2) solution containing ferricyanide, horse heart cytochrome C and 0.002028 Units of Aio.

This gave final concentrations of 14 micromolar ferricyanide, 100 nanomolar horse heart cytochrome C and either 0 ppb, 250 ppb, 500 ppb or 750 ppb arsenite. 60 seconds after mixing a chronoamperometry measurement was made by applying a step potential of 0.5 V vs Ag/AgCl reference electrode and recording data for 60 seconds.

Figure 6:
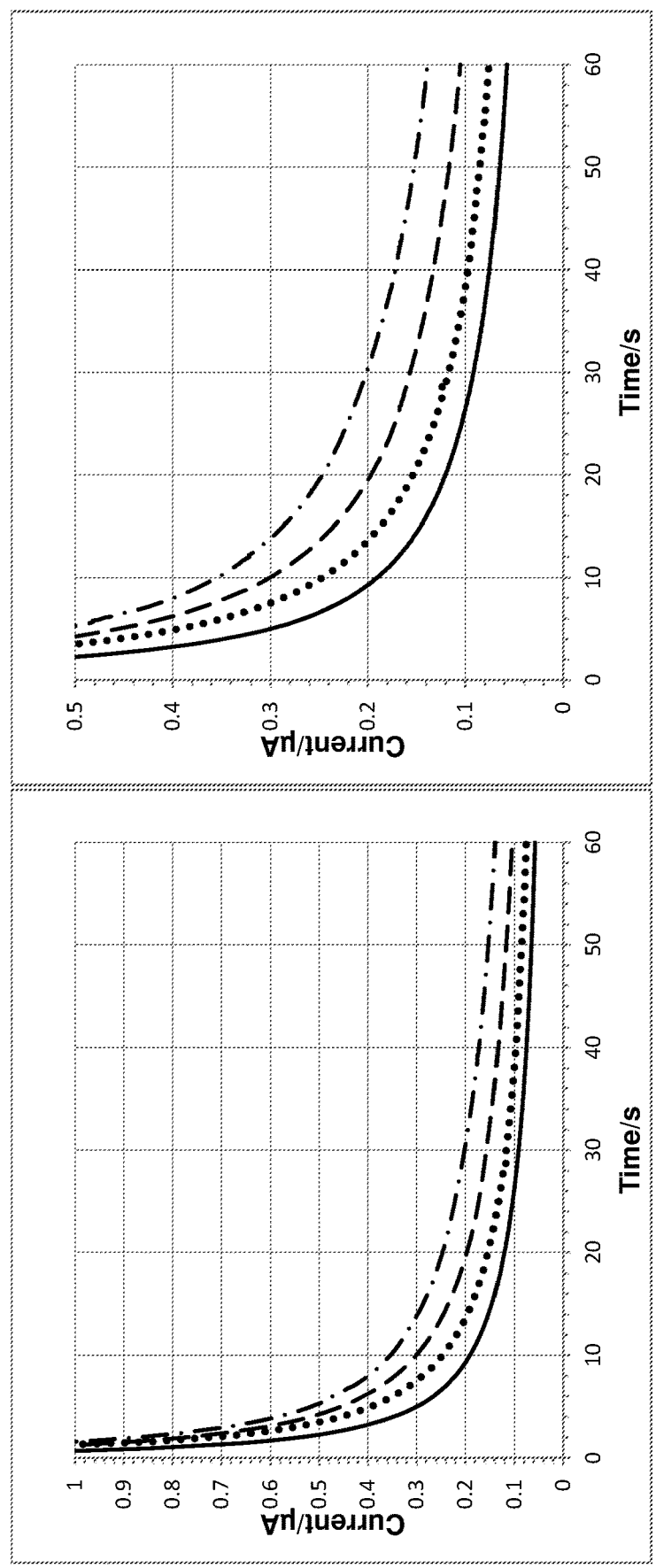
Figure 7:
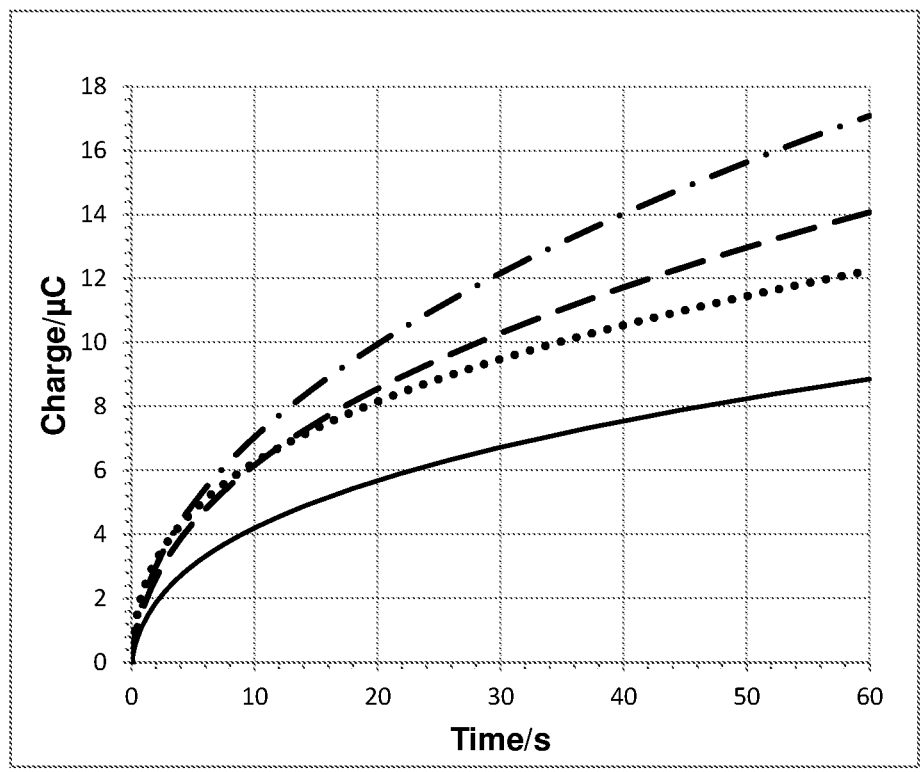
FIG. 7 shows a plot of the integration of the chronoamperometry data shown in FIGS. 6a and 6b.

The chronoamperometry results for experiment 3 are shown in FIGS. 6a and 6b. FIG. 6b is a magnified plot of FIG. 6a. FIG. 7 shows a plot of the integration of the chronoamperometry data shown in FIGS. 6a and 6b.

Figure 8:
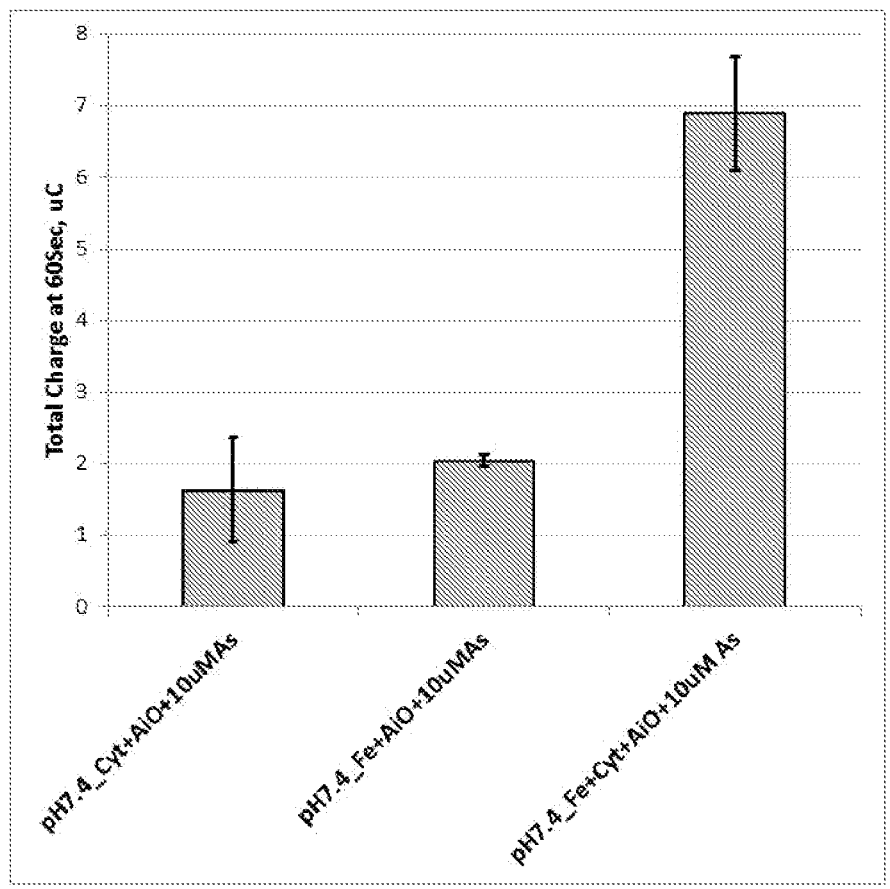
FIG. 8 is a graph showing the accumulative charge at 60 seconds for experiments 1, 2 and 3 using 750 ppb arsenite. Each experiment was conducted in triplicates. The dual mediator gave a ×3.5 increase in signal.

As clearly shown in FIG. 8, at pH 7.2 the dual mediator system more rapidly converts the final mediator (in experiment 3 this is ferricyanide) to the reduced form, so that when the reduced form is re-oxidised using chronoamperometry and the time-current curve is integrated, a higher charge value is observed.

Figure 9:
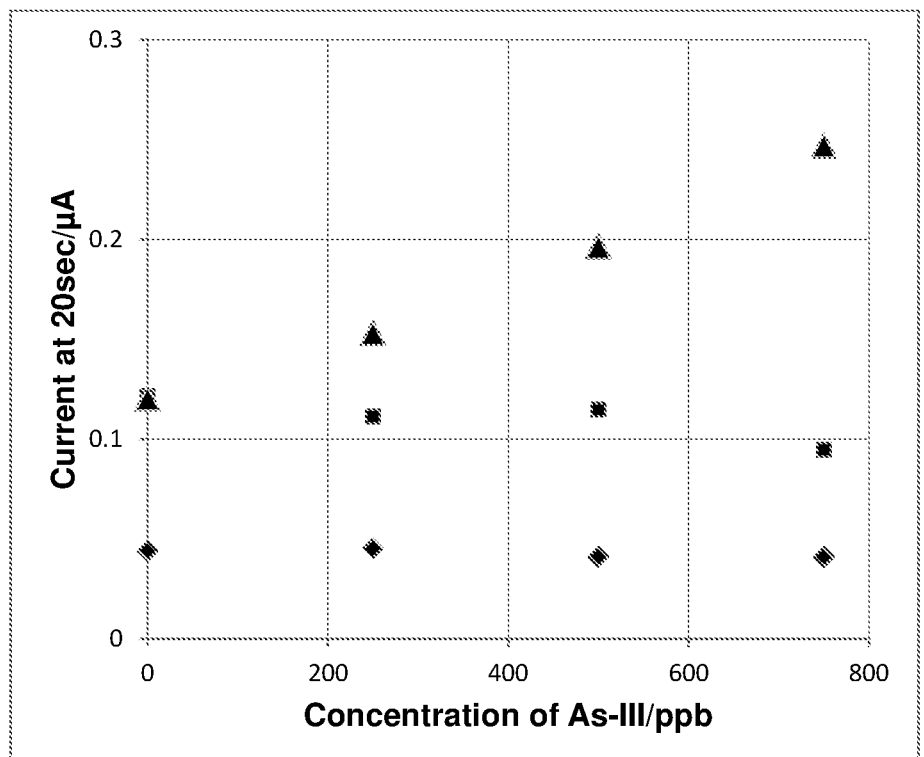
FIG. 9 is a graph showing a plot of the current at 20 seconds against concentration of arsenite (0 ppb, 250 ppb, 500 ppb and 750 ppb) for experiments 1, 2 and 3.

As clearly shown in FIG. 9, for single mediators there is very little increase in measured current with increasing arsenite concentration, while the dual mediator system produces a higher increase in current with increasing arsenite concentration. This provides an improved signal to noise ratio when measuring different concentrations of arsenite. The increase in current with increasing arsenite concentration enables rapid arsenic measurements to be made using the dual mediator system of the present invention.

The invention claimed is:

1. A device for detecting the presence of an analyte in a sample, comprising
   (i) at least one electrode,
   (ii) an arsenite oxidase enzyme, and
   (iii) first and second redox mediators:
      wherein the first and second redox mediators are each independently selected from compounds which exist in two or more different redox states, and are selected from iron, ruthenium, cobalt or osmium complexes;
      wherein the first and second redox mediators are different; and
      wherein the arsenite oxidase enzyme is a molybdenum-containing arsenite oxidase Aio from NT-26, or is derived from Aio from NT-26;
   wherein the arsenite oxidase enzyme is modified to prevent translocation to the periplasm, wherein the enzyme comprises the native AioA subunit from NT-26, or a variant, homologue or derivative thereof having at least 60% sequence identity to SEQ ID NO: 4, and the native AioB subunit from NT-26 or a variant, homologue or derivative thereof having at least 60% sequence identity to SEQ ID NO: 3, wherein a portion of the native AioB subunit corresponding to the translocation signal sequence, or a functional fragment thereof, is modified.

2. The device according to claim 1, wherein the electrode comprises one or more conducting materials selected from carbon, carbon nanotubes, graphene, graphite, gold, palladium, platinum, glassy carbon, nanoscale metal oxides and/or nanoscale metal.

3. The device according to claim 2, wherein the electrode is a metallic spluttered thin-film electrode made of gold, platinum or palladium.

4. The device according to claim 2, wherein the electrode is a thin film metallic electrode.

5. The device according to claim 1, wherein the first redox mediator accepts an electron from the enzyme and transfers an electron to the second redox mediator.

6. The device according to claim 1, wherein the first redox mediator is cytochrome C.

7. The device according to claim 1, wherein the second redox mediator accepts an electron from the first redox mediator and transfers an electron to the electrode.

8. The device according to claim 1, wherein the second redox mediator is ferricyanide or a lower potential iron complex.

9. The device according to claim 1, wherein the analyte is an arsenic derivative.

10. The device according to claim 1, wherein a portion of the native aioB gene which encodes the translocation signal sequence, or a portion thereof encoding a functional fragment of the translocation signal sequence, is modified.

11. The device according to claim 10, wherein the portion of the native aioB gene comprises the nucleotide sequence of SEQ ID NO. 6, or a homologue of SEQ ID NO. 6 encoding a functional fragment of the translocation signal sequence comprising the amino acid sequence of SEQ ID NO. 2.

12. The device of claim 1, wherein the modification is deletion.

13. The device of claim 1, wherein the AioB subunit comprises the peptide sequence of SEQ ID NO. 3, or a variant, homologue or derivative thereof having at least 60% identity to SEQ ID NO: 3, or is encoded by the polynucleotide sequence of SEQ ID NO. 7, or a variant, homologue or derivative thereof.

14. The device according to claim 10, wherein the AioA subunit comprises the peptide sequence of SEQ ID NO. 4, or a variant, homologue or derivative thereof having at least 60% identity to SEQ ID NO: 4, or is encoded by the polynucleotide sequence of SEQ ID NO. 8, or a variant, homologue or derivative thereof.

15. The device according to claim 1, further comprising a reference electrode.

16. The device according to claim 15, wherein the reference electrode comprises a Ag/AgCl reference redox couple.

17. The device according to claim 1, wherein the device is a test strip with a micro-structured surface.

18. The device according to claim 1, wherein the first and second redox mediators are each independently selected from ferrocene or ferrocene derivatives including ferrocene carboxylic acid, hydroxymethyl ferrocene (ferrocene methanol), and ferricyanide, tris(2,2'-bipyridine)dichlororuthenium(II) and cytochrome C, conducting organic polymers, conducting organic salts, tetrathiafulvalene (TTF) and/or quinones, and 2,6-dichlorophenolindophenol.

19. An electrochemical system comprising the device of claim 1.

20. A method of detecting the presence of arsenite in a sample, comprising contacting the device of claim 1 with the sample, thereby detecting arsenite in the sample when arsenite is present in the sample.

21. The method according to claim 20, wherein the sample is a liquid sample.

22. The method according to claim 20, wherein the sample has a neutral pH of around pH7.

* * * * *

UNITED STATES PATENT AND TRADEMARK OFFICE
CERTIFICATE OF CORRECTION

Page 1 of 1

PATENT NO. : 10,975,410 B2
APPLICATION NO. : 15/763654
DATED : April 13, 2021
INVENTOR(S) : Anthony Edward George Cass It is certified that error appears in the above-identified patent and that said Letters Patent is hereby corrected as shown below:

On the Title Page

(30) Foreign Application Priority Data: Please correct "1517275" to read -- 1517275.2 --

In the Specification

Column 2, Line 20: Please correct "SIP" to read -- $Sb^{III}$ --

Signed and Sealed this
Third Day of August, 2021

Drew Hirshfeld
*Performing the Functions and Duties of the
Under Secretary of Commerce for Intellectual Property and
Director of the United States Patent and Trademark Office*

SEQUENCE LISTING

<160> NUMBER OF SEQ ID NOS: 8

<210> SEQ ID NO 1
<211> LENGTH: 175
<212> TYPE: PRT
<213> ORGANISM: Rhizobium sp. NT-26

<400> SEQUENCE: 1

```
Met Ser Arg Cys Gln Asn Met Val Asp Ile Gly Arg Arg Gln Phe Leu
1               5                   10                  15

Arg Gly Gly Ala Leu Ala Ala Ala Gly Ala Thr Ala Ala Val Phe Gly
            20                  25                  30

Val Gly Ala Pro Gln Ala Arg Ala Ala Thr Ala Ala Gly Val Glu
        35                  40                  45

Tyr Pro Ala Asn Arg Leu Ala Asn Ile Ser Glu Leu Thr Leu Asn Glu
50                  55                  60

Pro Leu Asp Val Ala Tyr Pro Asp Glu Asp Ala Ala Gly Val Leu Leu
65                  70                  75                  80

Lys Leu Gly Thr Arg Val Glu Gly Gly Val Gly Pro Asp Gly Asp Ile
                85                  90                  95

Val Gly Phe Ser Thr Ile Cys Pro His Lys Gly Phe Pro Leu Ser Tyr
            100                 105                 110

Ser Ala Asp Asn Lys Thr Phe Asn Cys Pro Gly His Phe Ser Val Phe
            115                 120                 125

Asp Pro Glu Lys Gly Gly Gln Gln Val Trp Gly Gln Ala Thr Gln Asn
        130                 135                 140

Leu Pro Gln Tyr Val Leu Arg Val Ala Asp Asn Gly Asp Ile Phe Ala
145                 150                 155                 160

Glu Gly Val Asp Glu Leu Ile Tyr Gly Arg Leu Ser Asn Val Leu
                165                 170                 175

<210> SEQ ID NO 2
<211> LENGTH: 40
<212> TYPE: PRT
<213> ORGANISM: Rhizobium sp. NT-26

<400> SEQUENCE: 2

Met Ser Arg Cys Gln Asn Met Val Asp Ile Gly Arg Arg Gln Phe Leu
1               5                   10                  15

Arg Gly Gly Ala Leu Ala Ala Ala Gly Ala Thr Ala Ala Val Phe Gly
            20                  25                  30

Val Gly Ala Pro Gln Ala Arg Ala
        35                  40

<210> SEQ ID NO 3
<211> LENGTH: 150
<212> TYPE: PRT
<213> ORGANISM: Rhizobium sp. NT-26

<400> SEQUENCE: 3

Ala Thr Ala Ala Val Phe Gly Val Gly Ala Pro Gln Ala Arg Ala Ala
1               5                   10                  15

Thr Ala Ala Gly Val Glu Tyr Pro Ala Asn Arg Leu Ala Asn Ile
            20                  25                  30

Ser Glu Leu Thr Leu Asn Glu Pro Leu Asp Val Ala Tyr Pro Asp Glu
            35                  40                  45

Asp Ala Ala Gly Val Leu Leu Lys Leu Gly Thr Arg Val Glu Gly Gly
        50                  55                  60

Val Gly Pro Asp Gly Asp Ile Val Gly Phe Ser Thr Ile Cys Pro His
65                  70                  75                  80

Lys Gly Phe Pro Leu Ser Tyr Ser Ala Asp Asn Lys Thr Phe Asn Cys
                85                  90                  95

Pro Gly His Phe Ser Val Phe Asp Pro Glu Lys Gly Gly Gln Gln Val
            100                 105                 110
```

```
Trp Gly Gln Ala Thr Gln Asn Leu Pro Gln Tyr Val Leu Arg Val Ala
            115                 120                 125

Asp Asn Gly Asp Ile Phe Ala Glu Gly Val Asp Glu Leu Ile Tyr Gly
        130                 135                 140

Arg Leu Ser Asn Val Leu
145                 150

<210> SEQ ID NO 4
<211> LENGTH: 845
<212> TYPE: PRT
<213> ORGANISM: Rhizobium sp. NT-26

<400> SEQUENCE: 4

Met Ala Phe Lys Arg His Ile Asp Arg Leu Pro Ile Ile Pro Ala Asp
1               5                   10                  15

Ala Lys Lys His Asn Val Thr Cys His Phe Cys Ile Val Gly Cys Gly
            20                  25                  30

Tyr His Ala Tyr Thr Trp Pro Ile Asn Lys Gln Gly Gly Thr Asp Pro
        35                  40                  45

Gln Asn Asn Ile Phe Gly Val Asp Leu Ser Glu Gln Gln Ala Glu
    50                  55                  60

Ser Asp Ala Trp Tyr Ser Pro Ser Met Tyr Asn Val Val Lys Gln Asp
65                  70                  75                  80

Gly Arg Asp Val His Val Val Ile Lys Pro Asp His Glu Cys Val Val
                85                  90                  95

Asn Ser Gly Leu Gly Ser Val Arg Gly Ala Arg Met Ala Glu Thr Ser
            100                 105                 110

Phe Ser Glu Ala Arg Asn Thr Gln Gln Gln Arg Leu Thr Asp Pro Leu
        115                 120                 125

Val Trp Arg Tyr Gly Gln Met Gln Pro Thr Ser Trp Asp Asp Ala Leu
    130                 135                 140

Asp Leu Val Ala Arg Val Thr Ala Lys Ile Val Lys Glu Lys Gly Glu
145                 150                 155                 160

Asp Ala Leu Ile Val Ser Ala Phe Asp His Gly Gly Ala Gly Gly Gly
                165                 170                 175

Tyr Glu Asn Thr Trp Gly Thr Gly Lys Leu Tyr Phe Glu Ala Met Lys
            180                 185                 190

Val Lys Asn Ile Arg Ile His Asn Arg Pro Ala Tyr Asn Ser Glu Val
        195                 200                 205

His Gly Thr Arg Asp Met Gly Val Gly Glu Leu Asn Asn Cys Tyr Glu
    210                 215                 220

Asp Ala Glu Leu Ala Asp Thr Ile Val Ala Val Gly Thr Asn Ala Leu
225                 230                 235                 240

Glu Thr Gln Thr Asn Tyr Phe Leu Asn His Trp Ile Pro Asn Leu Arg
                245                 250                 255

Gly Glu Ser Leu Gly Lys Lys Lys Glu Leu Met Pro Glu Glu Pro His
            260                 265                 270

Glu Ala Gly Arg Ile Ile Ile Val Asp Pro Arg Arg Thr Val Thr Val
        275                 280                 285

Asn Ala Cys Glu Gln Thr Ala Gly Ala Asp Asn Val Leu His Leu Ala
    290                 295                 300

Ile Asn Ser Gly Thr Asp Leu Ala Leu Phe Asn Ala Leu Phe Thr Tyr
305                 310                 315                 320

Ile Ala Asp Lys Gly Trp Val Asp Arg Asp Phe Ile Asp Lys Ser Thr
                325                 330                 335
```

```
Leu Arg Glu Gly Thr Ala Arg Pro Leu Tyr Pro Ala Arg Gly Val
            340                 345                 350

Ser Glu Ala Asn Pro Gly His Leu Ser Ser Phe Glu Asp Ala Val Glu
            355                 360                 365

Gly Cys Arg Met Ser Ile Glu Glu Ala Ala Glu Ile Thr Gly Leu Asp
    370                 375                 380

Ala Ala Gln Ile Ile Lys Ala Ala Glu Trp Ile Gly Met Pro Lys Glu
385                 390                 395                 400

Gly Gly Lys Arg Arg Val Met Phe Gly Tyr Glu Lys Gly Leu Ile
                405                 410                 415

Trp Gly Asn Asp Asn Tyr Arg Thr Asn Gly Ala Leu Val Asn Leu Ala
            420                 425                 430

Leu Ala Thr Gly Asn Ile Gly Arg Pro Gly Gly Val Val Arg Leu
            435                 440                 445

Gly Gly His Gln Glu Gly Tyr Val Arg Pro Ser Asp Ala His Val Gly
    450                 455                 460

Arg Pro Ala Ala Tyr Val Asp Gln Leu Leu Ile Gly Gly Gln Gly Gly
465                 470                 475                 480

Val His His Ile Trp Gly Cys Asp His Tyr Lys Thr Thr Leu Asn Ala
                485                 490                 495

His Glu Phe Lys Arg Val Tyr Lys Lys Arg Thr Asp Met Val Lys Asp
            500                 505                 510

Ala Met Ser Ala Ala Pro Tyr Gly Asp Arg Glu Ala Met Val Asn Ala
            515                 520                 525

Ile Val Asp Ala Ile Asn Gln Gly Gly Leu Phe Ala Val Asn Val Asp
            530                 535                 540

Ile Ile Pro Thr Lys Ile Gly Glu Ala Cys His Val Ile Leu Pro Ala
545                 550                 555                 560

Ala Thr Ser Gly Glu Met Asn Leu Thr Ser Met Asn Gly Glu Arg Arg
                565                 570                 575

Met Arg Leu Thr Glu Arg Tyr Met Asp Pro Pro Gly Gln Ser Met Pro
            580                 585                 590

Asp Cys Leu Ile Ala Ala Arg Leu Ala Asn Thr Met Glu Arg Val Leu
            595                 600                 605

Thr Glu Met Gly Asp Val Gly Tyr Ala Ala Gln Phe Lys Gly Phe Asp
            610                 615                 620

Trp Gln Thr Glu Glu Asp Ala Phe Met Asp Gly Tyr Asn Lys Asn Ala
625                 630                 635                 640

His Gly Gly Glu Phe Val Thr Tyr Glu Arg Leu Ser Ala Met Gly Thr
                645                 650                 655

Asn Gly Phe Gln Glu Pro Ala Thr Gly Phe Thr Asp Gly Lys Ile Glu
            660                 665                 670

Gly Thr Gln Arg Leu Tyr Thr Asp Gly Val Phe Ser Thr Asp Asp Gly
            675                 680                 685

Lys Ala Arg Phe Met Asp Ala Pro Trp Arg Gly Leu Gln Ala Pro Gly
            690                 695                 700

Lys Gln Gln Gln Lys Asp Ser His Lys Tyr Leu Ile Asn Asn Gly Arg
705                 710                 715                 720

Ala Asn Val Val Trp Gln Ser Ala Tyr Leu Asp Gln Glu Asn Asp Phe
                725                 730                 735

Val Met Asp Arg Phe Pro Tyr Pro Phe Ile Glu Met Asn Pro Glu Asp
            740                 745                 750
```

```
Met Ala Glu Ala Gly Leu Lys Glu Gly Asp Leu Val Glu Ile Tyr Asn
            755                 760                 765
Asp Ala Gly Ala Thr Gln Ala Met Ala Tyr Pro Thr Pro Thr Ala Arg
        770                 775                 780
Arg Gly Glu Thr Phe Met Leu Phe Gly Phe Pro Thr Gly Val Gln Gly
785                 790                 795                 800
Asn Val Thr Ser Ala Gly Thr Asn Glu Leu Ile Ile Pro Asn Tyr Lys
                805                 810                 815
Gln Thr Trp Gly Asn Ile Arg Lys Ile Ser Asp Ala Pro Arg Asn Val
            820                 825                 830
Ala His Leu Ser Phe Lys Ser Lys Glu Tyr Gln Ser Ala
            835                 840                 845

<210> SEQ ID NO 5
<211> LENGTH: 528
<212> TYPE: DNA
<213> ORGANISM: Rhizobium sp. NT-26

<400> SEQUENCE: 5
atgtcacgtt gtcaaaacat ggtcgatatt ggccgacgcc agttcctgcg tggaggcgcg      60
ctcgcggctg cgggtgcgac tgccgccgtc ttcggcgtcg gcgcaccaca ggctagagcc     120
gctaccgcgg cggcaggggt cgaatatcct gccaatcgtc tggcaaacat ctcagaactt     180
acgctcaatg aaccgctcga tgtcgcctat ccggacgagg atgccgcagg cgttctgctt     240
aagcttggga cccgcgtcga gggtggcgtt ggccctgacg cgacattgt cggcttttcc      300 acgatctgtc ctcacaaggg ttttcctctg agctactccg ccgacaacaa gacgttcaac     360
tgtcctggtc acttctcggt cttcgaccct gaaaagggcg ccagcaggt ttggggtcag      420 gccacgcaga acctgccgca atacgtgctc cgcgtcgccg acaatggcga catctttgcc     480
gaaggcgtcg acgagctgat ctacggccgt ctgtccaacg ttctataa                  528

<210> SEQ ID NO 6
<211> LENGTH: 120
<212> TYPE: DNA
<213> ORGANISM: Rhizobium sp. NT-26

<400> SEQUENCE: 6
atgtcacgtt gtcaaaacat ggtcgatatt ggccgacgcc agttcctgcg tggaggcgcg      60
ctcgcggctg cgggtgcgac tgccgccgtc ttcggcgtcg gcgcaccaca ggctagagcc     120

<210> SEQ ID NO 7
<211> LENGTH: 408
<212> TYPE: DNA
<213> ORGANISM: Rhizobium sp. NT-26

<400> SEQUENCE: 7
gctaccgcgg cggcaggggt cgaatatcct gccaatcgtc tggcaaacat ctcagaactt      60
acgctcaatg aaccgctcga tgtcgcctat ccggacgagg atgccgcagg cgttctgctt     120
aagcttggga cccgcgtcga gggtggcgtt ggccctgacg cgacattgt cggcttttcc      180 acgatctgtc ctcacaaggg ttttcctctg agctactccg ccgacaacaa gacgttcaac     240
tgtcctggtc acttctcggt cttcgaccct gaaaagggcg ccagcaggt ttggggtcag      300 gccacgcaga acctgccgca atacgtgctc cgcgtcgccg acaatggcga catctttgcc     360
gaaggcgtcg acgagctgat ctacggccgt ctgtccaacg ttctataa                  408
```

<210> SEQ ID NO 8
<211> LENGTH: 2538
<212> TYPE: DNA
<213> ORGANISM: Rhizobium sp. NT-26

<400> SEQUENCE: 8

| | | | | | |
|---|---|---|---|---|---|
| atggccttca | aacgtcacat | cgaccgtctg | ccgatcattc | ccgcggacgc | caagaagcac | 60 |
| aatgtcacct | gccacttctg | catcgtcggt | tgcggctatc | acgcctatac | ctggccgatc | 120 |
| aacaaacaag | gcggtacgga | tccacagaac | aacatcttcg | gcgtcgacct | gtctgaacag | 180 |
| cagcaggcgg | aaagcgacgc | ctggtattca | ccgtccatgt | acaacgtggt | caagcaggat | 240 |
| ggccgcgacg | ttcatgtcgt | catcaagcca | gaccacgaat | gtgtcgtgaa | ctccggtctc | 300 |
| ggttcggtgc | gtggcgcccg | catggcagag | acgagcttct | cagaggcccg | caacacccag | 360 |
| cagcagcgcc | tcaccgatcc | gcttgtctgg | cgatacgggc | agatgcaacc | gacgagctgg | 420 |
| gacgacgcgc | tcgatctcgt | cgctcgcgtg | accgcgaaga | tcgtcaaaga | gaagggtgag | 480 |
| gacgccctca | tcgtatcggc | ctttgaccat | ggcggtgcag | gcggcggcta | cgagaacacc | 540 |
| tggggcacgg | gaaagctcta | tttcgaggcc | atgaaggtca | gaacatccg | catccacaac | 600 |
| cgccggcct | acaattccga | ggttcacggc | acccgcgaca | tgggcgtcgg | cgagttgaat | 660 |
| aactgctacg | aggatgccga | actggccgac | acgatcgttg | cggttggcac | caacgcgctg | 720 |
| gagacccaga | ccaactactt | cctaaatcac | tggattccga | atctgcgcgg | cgaaagcctc | 780 |
| ggcaagaaaa | aggagctcat | gccggaggag | ccccatgaag | caggcaggat | cattatcgtc | 840 |
| gatccgcgcc | gcaccgtgac | ggtcaatgcc | tgcgagcaga | cggccggcgc | cgacaatgtc | 900 |
| ctgcatcttg | ctatcaattc | tggcacggac | ctcgcccttt | tcaacgcact | cttcacctat | 960 |
| atcgccgaca | agggctgggt | cgatcgcgac | ttcatcgaca | agtcgacact | gcgcgagggt | 1020 |
| acagcccgac | cgccgctcta | tcctgcccgt | ggagtgtcag | aggccaatcc | ggggcatctc | 1080 |
| tcgagtttcg | aggacgccgt | ggaaggctgc | gcatgtcta | tcgaggaggc | tgcggaaatc | 1140 |
| accggtctcg | acgccgccca | gatcatcaag | gcagccgagt | ggatcggcat | gcccaaggaa | 1200 |
| ggcggcaagc | gccgccgtgt | catgttcggt | tacgagaagg | gtctgatctg | ggcaatgac | 1260 |
| aactaccgaa | ccaacggcgc | gctggtgaac | ctcgcccttg | ccaccggcaa | tatcggccgt | 1320 |
| cccggtggcg | cgtcgtacg | ccttggcgga | caccaggaag | gctatgtgcg | cccctccgac | 1380 |
| gcccatgtcg | gccggccggc | ggcctatgtc | gaccagttgc | tgatcggcgg | ccagggcggc | 1440 |
| gttcaccaca | tctggggctg | cgaccactac | aaaacgacgc | tcaatgcgca | tgagtttaag | 1500 |
| cgcgtctaca | agaagcgcac | cgacatggtg | aaggacgcca | tgagcgctgc | ccctacggc | 1560 |
| gaccgcgagg | ccatggtcaa | tgccattgtc | gacgcaatca | atcagggcgg | attgtttgcc | 1620 |
| gtcaatgtcg | acatcatccc | gacaaaaatc | ggcgaagcct | gtcatgttat | tctgcctgcg | 1680 |
| gccacgtcag | gcgagatgaa | cctcacgtca | atgaatggcg | agcggcgcat | gcggctgacc | 1740 |
| gaacgctata | tggaccccgcc | cggtcagtcc | atgccggact | gctgattgc | cgtcgtctc | 1800 |
| gccaacacca | tggaacgcgt | gctgaccgag | atgggtgacg | tcggctatgc | cgctcaattc | 1860 |
| aagggctttg | actggcagac | agaagaagac | gccttcatgg | acggctacaa | caagaatgca | 1920 |
| catggcggag | agttcgtcac | ctatgagcgc | ctgagtgcga | tgggcaccaa | cggcttccag | 1980 |
| gagccggcta | ccggctttac | cgacggcaag | atcgagggca | cccagcggct | ctataccgac | 2040 |
| ggcgtattct | cgaccgacga | cggcaaggcg | cggttcatgg | acgcgccatg | gcggggactt | 2100 |
| caggcaccgg | gcaagcagca | gcagaaggac | agccacaagt | acttgatcaa | caacggccgt | 2160 |

```
gccaatgtcg tctggcaatc ggcgtatctc gaccaggaaa acgacttcgt catggatcgt    2220
ttcccctacc cgttcatcga gatgaaccca gaggacatgg cggaagcagg ccttaaggag    2280
ggcgacctcg tcgagattta caatgatgcc ggagcgacgc aggccatggc ctatccgacg    2340
ccgacagccc gacgtggaga aaccttcatg ctgttcggtt ttccaaccgg ggttcagggc    2400
aatgtgacca gtgccgggac gaacgagttg ataatcccga actacaagca gacctggggc    2460
aatatccgca agatttcgga tgcgcccagg aacgtggctc acctttcctt caagtcgaaa    2520
gaataccagt cggcttga                                                  2538
```